US006143494A

United States Patent [19]
Kilpatrick

[11] Patent Number: 6,143,494

[45] **Date of Patent: *Nov. 7, 2000**

[54] POLIOVIRUS SPECIFIC PRIMERS AND METHODS OF DETECTION UTILIZING THE SAME

[75] Inventor: David R. Kilpatrick, Norcross, Ga.

[73] Assignee: The United States of America as represented by the Department of Health and Human Services, Washington, D.C.

[ * ] Notice: This patent is subject to a terminal disclaimer.

[21] Appl. No.: 08/935,100

[22] Filed: Sep. 25, 1997

Related U.S. Application Data

[63] Continuation of application No. 08/273,474, Jul. 11, 1994, Pat. No. 5,691,134, which is a continuation-in-part of application No. 08/092,110, Jul. 13, 1993.

[51] Int. Cl.[7] .............................. C12Q 1/70; C07H 21/02

[52] U.S. Cl. ............................................... 435/5; 536/23.1

[58] Field of Search .................... 435/5, 91.2; 536/23.1, 536/24.1

[56] References Cited

U.S. PATENT DOCUMENTS 5,691,134 11/1997 Kilpatrick .................................. 435/5

*Primary Examiner*—Eggerton A. Campbell
*Attorney, Agent, or Firm*—Fitch, Even, Tabin & Flannery

[57] ABSTRACT

The ability to rapidly detect wild polioviruses in clinical specimens is a major concern for the world-wide eradication of polioviruses. Provided is a method of detecting polioviruses of all three serotypes from viral isolates of clinical specimens using a pair of degenerate PCR primers. This primer set, which uses deoxyinosine residues to compensate for third position mismatches at specific positions, recognizes nucleotide sequences near the receptor binding site of polioviruses. These sequences are unique to polioviruses and are absolutely conserved at the amino acid level. As a result, these PCR primers do not recognize nonpoliovirus enteroviruses. All poliovirus serotypes (40 poliovaccine related genotypes and 120 wild poliovirus genotypes from around the world) tested positive. All 14 prototype strains of nonpoliovirus enteroviruses tested negative. Also provided is a series of degenerate PCR primers that differentiates between the three wild poliovirus serotypes and a method of detecting the presence of the three serotypes utilizing a nucleic acid amplification technique.

14 Claims, No Drawings

SEQUENCE LISTING (1) GENERAL INFORMATION:

(iii) NUMBER OF SEQUENCES: 35

(2) INFORMATION FOR SEQ ID NO:1:

(i) SEQUENCE CHARACTERISTICS:
       (A) LENGTH: 20 base pairs
       (B) TYPE: nucleic acid
       (C) STRANDEDNESS: single
       (D) TOPOLOGY: linear (ii) MOLECULE TYPE: Other nucleic acid (iv) ANTI-SENSE: YES (ix) FEATURE:
       (A) NAME/KEY: misc_feature
       (B) LOCATION: 1..20
       (D) OTHER INFORMATION: /product= "Synthetic DNA"
           /note= "In the primer sequence submitted
           N=deoxyinosine residues;
           R=A or G; and nucleotide (xi) SEQUENCE DESCRIPTION: SEQ ID NO:1:

TTNANNGCRT GNCCRTTRTT                                                20

(2) INFORMATION FOR SEQ ID NO:2:

(i) SEQUENCE CHARACTERISTICS:
       (A) LENGTH: 20 base pairs
       (B) TYPE: nucleic acid
       (C) STRANDEDNESS: single
       (D) TOPOLOGY: linear (ii) MOLECULE TYPE: Other nucleic acid (iv) ANTI-SENSE: NO (ix) FEATURE:
       (A) NAME/KEY: misc_feature
       (B) LOCATION: 1..20
       (D) OTHER INFORMATION: /product= "Synthetic DNA"
           /note= "In the primer sequence submitted
           N=deoxyinosine residues;
           M=A or C; Y=T or C; and (xi) SEQUENCE DESCRIPTION: SEQ ID NO:2:

TTCACMTANT CNMGNTTYGA                                                20

(2) INFORMATION FOR SEQ ID NO:3:

(i) SEQUENCE CHARACTERISTICS:
       (A) LENGTH: 7 amino acids
       (B) TYPE: amino acid
       (C) STRANDEDNESS: single
       (D) TOPOLOGY: linear (ii) MOLECULE TYPE: peptide (xi) SEQUENCE DESCRIPTION: SEQ ID NO:3:

Asn Asn Gly His Ala Leu Asn
1               5

(2) INFORMATION FOR SEQ ID NO:4:

(i) SEQUENCE CHARACTERISTICS:
       (A) LENGTH: 7 amino acids
       (B) TYPE: amino acid (C) STRANDEDNESS: single
            (D) TOPOLOGY: linear (ii) MOLECULE TYPE: peptide (xi) SEQUENCE DESCRIPTION: SEQ ID NO:4:

Phe Thr Tyr Ser Arg Phe Asp
1               5

(2) INFORMATION FOR SEQ ID NO:5:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: Other nucleic acid (iv) ANTI-SENSE: YES (ix) FEATURE:
            (A) NAME/KEY: misc_feature
            (B) LOCATION: 1..20
            (D) OTHER INFORMATION: /product= "Synthetic DNA"
                /note= "In the primer sequence submitted
                N=deoxyinosine residues;
                and nucleotide # for the (xi) SEQUENCE DESCRIPTION: SEQ ID NO:5:

TTNANNGCGT GNCCGTTGTT                                                     20

(2) INFORMATION FOR SEQ ID NO:6:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: Other nucleic acid (iv) ANTI-SENSE: YES (ix) FEATURE:
            (A) NAME/KEY: misc_feature
            (B) LOCATION: 1..20
            (D) OTHER INFORMATION: /product= "Synthetic DNA"
                /note= "In the primer sequence submitted
                N=deoxyinosine residues;
                and nucleotide # for the (xi) SEQUENCE DESCRIPTION: SEQ ID NO:6:

TTNANNGCAT GNCCGTTGTT                                                     20

(2) INFORMATION FOR SEQ ID NO:7:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: Other nucleic acid (iv) ANTI-SENSE: YES (ix) FEATURE:
            (A) NAME/KEY: misc_feature
            (B) LOCATION: 1..20
            (D) OTHER INFORMATION: /product= "Synthetic DNA"
                /note= "In the primer sequence submitted
                N=deoxyinosine residues;

```
                      and nucleotide # for the (xi) SEQUENCE DESCRIPTION: SEQ ID NO:7:

TTNANNGCAT GNCCATTGTT                                          20

(2) INFORMATION FOR SEQ ID NO:8:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: Other nucleic acid (iv) ANTI-SENSE: YES (ix) FEATURE:
        (A) NAME/KEY: misc_feature
        (B) LOCATION: 1..20
        (D) OTHER INFORMATION: /product= "Synthetic DNA"
            /note= "In the primer sequence submitted
            N=deoxyinosine residues;
            and nucleotide # for the (xi) SEQUENCE DESCRIPTION: SEQ ID NO:8:

TTNANNGCAT GNCCATTATT                                          20

(2) INFORMATION FOR SEQ ID NO:9:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: Other nucleic acid (iv) ANTI-SENSE: YES (ix) FEATURE:
        (A) NAME/KEY: misc_feature
        (B) LOCATION: 1..20
        (D) OTHER INFORMATION: /product= "Synthetic DNA"
            /note= "In the primer sequence submitted
            N=deoxyinosine residues;
            and nucleotide # for the (xi) SEQUENCE DESCRIPTION: SEQ ID NO:9:

TTNANNGCGT GNCCATTGTT                                          20

(2) INFORMATION FOR SEQ ID NO:10:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: Other nucleic acid (iv) ANTI-SENSE: YES (ix) FEATURE:
        (A) NAME/KEY: misc_feature
        (B) LOCATION: 1..20
        (D) OTHER INFORMATION: /product= "Synthetic DNA"
            /note= "In the primer sequence submitted
            N=deoxyinosine residues;
            and nucleotide # for the (xi) SEQUENCE DESCRIPTION: SEQ ID NO:10:
```

```
TTNANNGCGT GNCCATTATT                                              20
```

(2) INFORMATION FOR SEQ ID NO:11:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: Other nucleic acid (iv) ANTI-SENSE: YES (ix) FEATURE:
        (A) NAME/KEY: misc_feature
        (B) LOCATION: 1..20
        (D) OTHER INFORMATION: /product= "Synthetic DNA"
            /note= "In the primer sequence submitted
            N=deoxyinosine residues;
            and nucleotide # for the (xi) SEQUENCE DESCRIPTION: SEQ ID NO:11:

```
TTNANNGCGT GNCCGTTATT                                              20
```

(2) INFORMATION FOR SEQ ID NO:12:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(iv) ANTI-SENSE: YES (ix) FEATURE:
        (A) NAME/KEY: misc_feature
        (B) LOCATION: 1..20
        (D) OTHER INFORMATION: /product= "Synthetic DNA"
            /note= "In the primer sequence submitted
            N=deoxyinosine residues;
            and nucleotide # for the (xi) SEQUENCE DESCRIPTION: SEQ ID NO:12:

```
TTNANNGCAT GNCCGTTATT                                              20
```

(2) INFORMATION FOR SEQ ID NO:13:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: Other nucleic acid (iv) ANTI-SENSE: NO (ix) FEATURE:
        (A) NAME/KEY: misc_feature
        (B) LOCATION: 1..20
        (D) OTHER INFORMATION: /product= "Synthetic DNA"
            /note= "In the primer sequence submitted
            N=deoxyinosine residues;
            and nucleotide # for the (xi) SEQUENCE DESCRIPTION: SEQ ID NO:13:

```
TTCACATANT CNAGNTTTGA                                              20
```

(2) INFORMATION FOR SEQ ID NO:14:

(i) SEQUENCE CHARACTERISTICS:
    (A) LENGTH: 20 base pairs
    (B) TYPE: nucleic acid
    (C) STRANDEDNESS: single
    (D) TOPOLOGY: linear (ii) MOLECULE TYPE: Other nucleic acid (iv) ANTI-SENSE: NO (ix) FEATURE:
    (A) NAME/KEY: misc_feature
    (B) LOCATION: 1..20
    (D) OTHER INFORMATION: /product= "Synthetic DNA"
        /note= "In the primer sequence submitted
        N=deoxyinosine residues;
        and nucleotide # for the (xi) SEQUENCE DESCRIPTION: SEQ ID NO:14:

TTCACCTANT CNAGNTTTGA                                               20

(2) INFORMATION FOR SEQ ID NO:15:

(i) SEQUENCE CHARACTERISTICS:
    (A) LENGTH: 20 base pairs
    (B) TYPE: nucleic acid
    (C) STRANDEDNESS: single
    (D) TOPOLOGY: linear (ii) MOLECULE TYPE: Other nucleic acid (iv) ANTI-SENSE: NO (ix) FEATURE:
    (A) NAME/KEY: misc_feature
    (B) LOCATION: 1..20
    (D) OTHER INFORMATION: /product= "Synthetic DNA"
        /note= "In the primer sequence submitted
        N=deoxyinosine residues;
        and nucleotide # for the (xi) SEQUENCE DESCRIPTION: SEQ ID NO:15:

TTCACATANT CNCGNTTTGA                                               20

(2) INFORMATION FOR SEQ ID NO:16:

(i) SEQUENCE CHARACTERISTICS:
    (A) LENGTH: 20 base pairs
    (B) TYPE: nucleic acid
    (C) STRANDEDNESS: single
    (D) TOPOLOGY: linear (ii) MOLECULE TYPE: Other nucleic acid (iv) ANTI-SENSE: NO (ix) FEATURE:
    (A) NAME/KEY: misc_feature
    (B) LOCATION: 1..20
    (D) OTHER INFORMATION: /product= "Synthetic DNA"
        /note= "In the primer sequence submitted
        N=deoxyinosine residues;
        and nucleotide # for the (xi) SEQUENCE DESCRIPTION: SEQ ID NO:16:

TTCACATANT CNCGNTTCGA                                               20

(2) INFORMATION FOR SEQ ID NO:17:

(i) SEQUENCE CHARACTERISTICS:
    (A) LENGTH: 20 base pairs
    (B) TYPE: nucleic acid (C) STRANDEDNESS: single
            (D) TOPOLOGY: linear (ii) MOLECULE TYPE: Other nucleic acid (ix) FEATURE:
            (A) NAME/KEY: misc_feature
            (B) LOCATION: 1..20
            (D) OTHER INFORMATION: /product= "Synthetic DNA"
                /note= "In the primer sequence submitted
                N=deoxyinosine residues;
                and nucleotide # for the (xi) SEQUENCE DESCRIPTION: SEQ ID NO:17:

TTCACATANT CNAGNTTCGA                                               20

(2) INFORMATION FOR SEQ ID NO:18:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: Other nucleic acid (iv) ANTI-SENSE: NO (ix) FEATURE:
            (A) NAME/KEY: misc_feature
            (B) LOCATION: 1..20
            (D) OTHER INFORMATION: /product= "Synthetic DNA"
                /note= "In the primer sequence submitted
                N=deoxyinosine residues;
                and nucleotide # for the (xi) SEQUENCE DESCRIPTION: SEQ ID NO:18:

TTCACCTANT CNCGNTTTGA                                               20

(2) INFORMATION FOR SEQ ID NO:19:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: Other nucleic acid (iv) ANTI-SENSE: NO (ix) FEATURE:
            (A) NAME/KEY: misc_feature
            (B) LOCATION: 1..20
            (D) OTHER INFORMATION: /product= "Synthetic DNA"
                /note= "In the primer sequence submitted
                N=deoxyinosine residues;
                and nucleotide # for the (xi) SEQUENCE DESCRIPTION: SEQ ID NO:19:

TTCACCTANT CNCGNTTCGA                                               20

(2) INFORMATION FOR SEQ ID NO:20:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: Other nucleic acid (iv) ANTI-SENSE: NO

```
    (ix) FEATURE:
         (A) NAME/KEY: misc_feature
         (B) LOCATION: 1..20
         (D) OTHER INFORMATION: /product= "Synthetic DNA"
             /note= "In the primer sequence submitted
             N=deoxyinosine residues;
             and nucleotide # for the (xi) SEQUENCE DESCRIPTION: SEQ ID NO:20:

TTCACCTANT CNAGNTTCGA                                              20

(2) INFORMATION FOR SEQ ID NO:21:

(i) SEQUENCE CHARACTERISTICS:
         (A) LENGTH: 20 base pairs
         (B) TYPE: nucleic acid
         (C) STRANDEDNESS: single
         (D) TOPOLOGY: linear (ii) MOLECULE TYPE: Other nucleic acid (iv) ANTI-SENSE: NO (ix) FEATURE:
         (A) NAME/KEY: misc_feature
         (B) LOCATION: 1..20
         (D) OTHER INFORMATION: /product= "Synthetic DNA"
             /note= "At position #2860 and position #2863
             N=deoxyinosine residues;
             at position #2866 N=

(xi) SEQUENCE DESCRIPTION: SEQ ID NO:21:

TTCACMTANT CNAGNTTTGA                                              20

(2) INFORMATION FOR SEQ ID NO:22:

(i) SEQUENCE CHARACTERISTICS:
         (A) LENGTH: 19 base pairs
         (B) TYPE: nucleic acid
         (C) STRANDEDNESS: single
         (D) TOPOLOGY: linear (ii) MOLECULE TYPE: Other nucleic acid (iv) ANTI-SENSE: NO (ix) FEATURE:
         (A) NAME/KEY: misc_feature
         (B) LOCATION: 1..19
         (D) OTHER INFORMATION: /product= "Synthetic DNA"
             /note= "In the primer sequence submitted
             N=deoxyinosine residues;
             Y=T or C; and nucleotide (xi) SEQUENCE DESCRIPTION: SEQ ID NO:22:

TGCGNGAYAC NACNCAYAT                                               19

(2) INFORMATION FOR SEQ ID NO:23:

(i) SEQUENCE CHARACTERISTICS:
         (A) LENGTH: 20 base pairs
         (B) TYPE: nucleic acid
         (C) STRANDEDNESS: single
         (D) TOPOLOGY: linear (ii) MOLECULE TYPE: Other nucleic acid (iv) ANTI-SENSE: YES (ix) FEATURE:
         (A) NAME/KEY: misc_feature
         (B) LOCATION: 1..20
```

(D) OTHER INFORMATION: /product= "Synthetic DNA"
            /note= "In the primer sequence submitted
            N=deoxyinosine residues;
            R=A or G; Y=T or C; and (xi) SEQUENCE DESCRIPTION: SEQ ID NO:23:

CGNACNGTRY TRTCNATCAT                                                   20

(2) INFORMATION FOR SEQ ID NO:24:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: Other nucleic acid (iv) ANTI-SENSE: NO (ix) FEATURE:
        (A) NAME/KEY: misc_feature
        (B) LOCATION: 1..20
        (D) OTHER INFORMATION: /product= "Synthetic DNA"
            /note= "In the primer sequence submitted
            N=deoxyinosine residues;
            Y=T or C; S=G or C; and (xi) SEQUENCE DESCRIPTION: SEQ ID NO:24:

GTNNSNGCNT GYAAYGAYTT                                                   20

(2) INFORMATION FOR SEQ ID NO:25:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: Other nucleic acid (iv) ANTI-SENSE: YES (ix) FEATURE:
        (A) NAME/KEY: misc_feature
        (B) LOCATION: 1..20
        (D) OTHER INFORMATION: /product= "Synthetic DNA"
            /note= "In the primer sequence submitted
            N=deoxyinosine residues;
            R=A or G; Y=T or C; and (xi) SEQUENCE DESCRIPTION: SEQ ID NO:25:

AYNCCYTCNA CNRCNCCYTC                                                   20

(2) INFORMATION FOR SEQ ID NO:26:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: Other nucleic acid (iv) ANTI-SENSE: NO (ix) FEATURE:
        (A) NAME/KEY: misc_feature
        (B) LOCATION: 1..20
        (D) OTHER INFORMATION: /product= "Synthetic DNA"
            /note= "In the primer sequence submitted
            N=deoxyinosine residues;
            Y=T or C; and nucleotide (xi) SEQUENCE DESCRIPTION: SEQ ID NO:26:

AAYCCNTCNA TNTTYTAYAC                                                    20

(2) INFORMATION FOR SEQ ID NO:27:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: Other nucleic acid (iv) ANTI-SENSE: YES (ix) FEATURE:
            (A) NAME/KEY: misc_feature
            (B) LOCATION: 1..20
            (D) OTHER INFORMATION: /product= "Synthetic DNA"
                /note= "In the primer sequence submitted
                N=deoxyinosine residues;
                R=A or G; Y=T or C; K=G (xi) SEQUENCE DESCRIPTION: SEQ ID NO:27:

CCNANYTGRT CATTNKCRTC                                                    20

(2) INFORMATION FOR SEQ ID NO:28:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: Other nucleic acid (iv) ANTI-SENSE: YES (ix) FEATURE:
            (A) NAME/KEY: misc_feature
            (B) LOCATION: 1..20
            (D) OTHER INFORMATION: /product= "Synthetic DNA"
                /note= "In the primer sequence submitted
                N=deoxyinosine residues;
                R=A or G; Y=T OR C; and (xi) SEQUENCE DESCRIPTION: SEQ ID NO:28:

ARNGCNCYYT GNGCNACNTC                                                    20

(2) INFORMATION FOR SEQ ID NO:29:

(i) SEQUENCE CHARACTERISTICS:
            (A) LENGTH: 7 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:29:

Met Ile Asp Asn Thr Val Arg
1               5

(2) INFORMATION FOR SEQ ID NO:30:

(i) SEQUENCE CHARACTERISTICS:
            (A) LENGTH: 7 amino acids
            (B) TYPE: amino acid
            (C) STRANDEDNESS: single
            (D) TOPOLOGY: linear

```
        (ii) MOLECULE TYPE: peptide (xi) SEQUENCE DESCRIPTION: SEQ ID NO:30:

Glu Gly Val Val Glu Gly Val
1               5

(2) INFORMATION FOR SEQ ID NO:31:

(i) SEQUENCE CHARACTERISTICS:
            (A) LENGTH: 7 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:31:

Glu Val Ala Gln Gly Ala Leu
1               5

(2) INFORMATION FOR SEQ ID NO:32:

(i) SEQUENCE CHARACTERISTICS:
            (A) LENGTH: 7 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:32:

Asp Ala Asn Asp Gln Ile Gly
1               5

(2) INFORMATION FOR SEQ ID NO:33:

(i) SEQUENCE CHARACTERISTICS:
            (A) LENGTH: 7 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:33:

Leu Arg Asp Thr Thr His Ile
1               5

(2) INFORMATION FOR SEQ ID NO:34:

(i) SEQUENCE CHARACTERISTICS:
            (A) LENGTH: 7 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:34:

Val Ser Ala Cys Asn Asp Phe
1               5

(2) INFORMATION FOR SEQ ID NO:35:

(i) SEQUENCE CHARACTERISTICS:
            (A) LENGTH: 7 amino acids
            (B) TYPE: amino acid
            (C) STRANDEDNESS: single
```

-continued

```
         (D) TOPOLOGY: linear (ii) MOLECULE TYPE: peptide (xi) SEQUENCE DESCRIPTION: SEQ ID NO:35:

Asn Pro Ser Ile Phe Tyr Thr
1               5
```

POLIOVIRUS SPECIFIC PRIMERS AND METHODS OF DETECTION UTILIZING THE SAME

This application is a continuation of Ser. No. 08/273,474 filed on Jul. 11, 1994, U.S. Pat. No. 5,691,134 which was a continuation in part of Ser. No. 08/092,110 filed on Jul. 13, 1993.

BACKGROUND OF THE INVENTION

1. Field of the Invention

This invention relates to polioviruses. In particular, this invention relates to poliovirus specific primers for detection of polioviruses in clinical samples.

2. Background Art

A worldwide endeavor sponsored by the World Health Organization is underway to eradicate all wild polioviruses by the year 2000, and virologic surveillance is therefore critical to this eradication goal. In 1990, an estimated 150,000 cases of poliomyelitis were occurring annually in 70 countries where the disease is still endemic. One of the primary goals to the global eradication of poliomyelitis by the year 2000 is in the intensive surveillance of acute flaccid paralysis (AFP) which can be caused by poliovirus. This is especially true in the Americas where the spread of the wild poliovirus has ceased for a period of at least two years. Nevertheless, 2400 cases of AFP in the first 40 weeks of 1992 needed to be screened for poliovirus. Of the 60 poliovirus related cases (3% of the total), none were the wild-type virus. Twenty percent (20%) of the total cases were found to be other non-polio enteroviruses (NPEV) and the remaining cases (76%) were negative for enteroviruses. Since the surveillance of wild-type poliovirus in AFP cases must be maintained at high levels, a detection system that would identify all polioviruses rapidly to the exclusion of NPEV is needed.

NPEVs also cause a wide range of diseases in addition to AFP and the ability to distinguish these cases from vaccine-related poliovirus cases would also be very beneficial. Currently, differentiation of poliovirus from nonpoliovirus is done by limited neutralization using three types of poliovirus antisera. This procedure is time consuming and sometimes has difficulties in identifying isolates containing mixtures of poliovirus and nonpoliovirus.

Poliovirus genomes evolve rapidly during replication in humans (Nottay et al., 1981; Minor et al., 1982). As a result, the nucleotide sequences of wild polioviruses currently in circulation throughout the world are extremely heterogeneous Russ-Hess et al., 1987; Kew et al., 1990a). A typical rate for the fixation of mutations over the entire genome is one to two nucleotide substitutions per week (Nottay, et al., 1981). Although there may be a high degree of conservation at the amino acid level, there is considerable nucleotide variation. This variability occurs primarily by mutation to synonymous codons (Parvin et al., 1986), while immune selection pressures are responsible for some of this variability (Diamond et al., 1985; Blondel et al., 1986; Weigers and Dernick, 1992).

Independent wild poliovirus genotypes are usually geographically restricted (Kew et al., 1990a) and as a result, periodic epidemics involve the clonal expansion of this one restricted lineage. PCR primer sets for several wild poliovirus genotypes from the American regions have been previously described (Pan American Health Organization, 1990; Kew et al., 1990b; de Quadros et al., 1991; Yang et al., 1992). Similarly, primers have been developed which identify vaccine and reference strains of poliovirus (Yang et al., 1991; and Balanant et al., 1991). However, the molecular reagents currently in use do not allow for the rapid detection of all wild poliovirus genotypes in a single assay. Most of the PCR assays previously developed to detect either picornaviruses in general (Hyypia et al., 1989; Chapman et al., 1990; Olive et al., 1990), or polioviruses specifically (Abraham et al., 1993) have targeted conserved sequences within the 5' noncoding region. PCR primers that are specific for the 5' noncoding region are subject to possible intertypic recombination, and therefore are not applicable to worldwide detection of polioviruses due to potential crossover problems. A large proportion of vaccine-related clinical isolates are intertypic recombinants (Kew and Nottay, 1984; Minor et al., 1986a).

Until genotype-specific primers and probes can be developed for all endemic wild polioviruses, a single specific assay system is needed that 1) detects wild poliovirus genotypes, from all geographic regions, including possibly undetermined geographic regions, and 2) distinguishes NPEV infections from poliovirus infections. The ability to differentiate between poliovirus and NPEV infections is of particular importance in those regions (such as the Americas) that no longer have wild poliovirus infections, but continue to have paralytic cases due to NPEVs.

Accordingly, the present invention provides a degenerate PCR primer designed to identify all three poliovirus serotypes, while not recognizing NPEVs. The primers of the present invention are specific for polioviruses, therefore excluding all other known viruses from detection. In addition to being specific for polioviruses, the primers of the present invention are capable of detecting all poliovirus strains so far tested in all three known serotypes.

The poliovirus-specific PCR primers and methods of detection of the present invention will allow for the rapid determination of whether clinical cases of acute flaccid paralysis are the result of a polio virus infection. Therefore, this invention meets an immediate need in the worldwide poliomyelitis eradication program, since these "pan-poliovirus" primers detect all genotypes of wild and vaccine related polioviruses.

Because periodic epidemics of independent poliovirus genotypes involves clonal expansion of restricted lineages, there also exists a need to effectively track the expansion of individual serotypes of poliovirus. The molecular reagents currently in use do not allow for the rapid differentiation of individual wild poliovirus serotypes in a single assay. Serotyping is presently done using serotype-specific antisera in a micro-neutralization assay, which is time-consuming and has rather a low sensitivity level compared to molecular based methods.

Therefore, a need exists serotype-specific primers and probes can be developed for the three known serotypes of poliovirus, a for a method to rapidly distinguish between the poliovirus serotypes in order to 1) improve the speed of processing large numbers of clinical samples, and 2) increase the sensitivity of detecting minority populations of poliovirus in mixed serotype cultures.

Accordingly, the present invention provides a series of PCR primers that differentiate between the three wild poliovirus serotypes. Several sequences were identified as possible PCR primer sites after searching the poliovirus VP1 amino acid alignments that are contained in the CDC (The Centers for Disease Control and Prevention) poliovirus sequence database. Additionally, empirical evidence obtained through experimentation provided data that identified the specific degenerate PCR primers designed to identify these conserved amino acid stretches. The primers of the present invention are specific for polioviruses, therefore excluding all other known viruses from detection. In addition to being specific for polioviruses, the primers of the present invention are capable of detecting all poliovirus strains so far tested in all three known serotypes.

The sero-specific poliovirus PCR primers and methods of detection of the present invention will allow for the rapid determination of whether clinical cases of acute flaccid paralysis are the result of a polio virus infection, and allow researchers to track the spread or migration of specific poliovirus serotypes. Therefore, this invention meets an immediate need in the worldwide poliomyelitis eradication program, since these "sero-specific" poliovirus primers detect and distinguish all serotypes of wild and vaccine related polioviruses.

SUMMARY OF THE INVENTION

The present invention provides isolated synthetic nucleic acids designed to be specific and sensitive for detecting all genotypes of poliovirus. Isolated nucleic acids complementary to the nucleic acids of the present invention are also provided. The present invention also provides compositions comprising the nucleic acids of the invention and nucleic acids capable of selectively hybridizing therewith.

The present invention also provides isolated synthetic nucleic acids designed to be specific and sensitive for detecting and distinguishing the three serotypes of poliovirus. Isolated nucleic acids complementary to the nucleic acids of the present invention are also provided. The present invention also provides nucleic acids which selectively hybridize with the nucleic acids which are complementary to the synthetic nucleic acids of the invention.

The nucleic acids of the present invention can be utilized as degenerate primers and probes for the detection of a poliovirus in a sample utilizing a nucleic acid amplification technique. A method is also provided for detecting the presence or absence of a poliovirus in a sample containing nucleic acids which comprises amplifying the nucleic acids from the sample with the nucleic acids of the present invention and determining the presence or absence of nucleic acid from poliovirus, thereby detecting the presence or absence of poliovirus in the sample. Further contemplated is a kit for detecting the nucleic acid of a poliovirus comprising primers comprised of nucleic acids provided by the present invention.

Nucleic acids of the present invention can also be utilized as degenerate primers and probes for the detection and identification of a specific poliovirus serotype in a sample utilizing a nucleic acid amplification technique. A method is also provided for detecting the presence or absence of a poliovirus serotype in a sample containing nucleic acids which comprises amplifying the nucleic acids from the sample with the nucleic acids of the present invention and determining the presence or absence of nucleic acid from poliovirus, thereby detecting the presence or absence of a specific poliovirus serotype in the sample. Further provided is a kit for detecting the nucleic acid of a poliovirus comprising primers comprised of nucleic acids provided by the present invention.

DESCRIPTION OF THE PREFERRED EMBODIMENTS

The present invention may be understood more readily by reference to the following detailed description of specific embodiments and the Examples, Tables and Sequence Listing included therein.

As used in the application, "a" can mean one or more, depending on the context with which it is used. The acronym "PCR" is used interchangeably with "polymerase chain reaction." The acronym "RT/PCR" is used interchangeably with "reverse transcriptase-polymerase chain reaction."

The present invention provides an isolated nucleic acid comprising the nucleotide sequence set forth in the Sequence Listing as SEQ ID NO:1. The consensus sequence set forth in SEQ ID NO:1 denotes the possible combinations of nucleotides that are found in SEQ ID NOS:5–12.

The present invention also provides an isolated nucleic acid which selectively hybridizes with a nucleic acid which is complementary to the nucleotide sequence set forth in the Sequence Listing as SEQ ID NO:1. When used to refer to nucleic acids which selectively hybridize with a nucleic acid which is complementary to the nucleotide sequence set forth in SEQ ID NO:1, "selectively hybridizing" means that the nucleic acid does not hybridize with sequences from other enteroviruses so as to prevent adequate positive hybridization with nucleic acids from a poliovirus.

The synthetic nucleic acids comprised of the nucleotide sequences set forth in the Sequence Listing also "selectively hybridize" with and amplify relevant portions from which they are derived. For example, the synthetic nucleic acids comprising the nucleotide sequences set forth in the Sequence Listing as SEQ ID NO:1 and SEQ IN NO:2 selectively hybridize with conserved regions of the poliovirus VP1 genome. When used in this context, "selectively hybridize" means that the synthetic nucleic acids (e.g., SEQ ID NOS:1 and 2) do not hybridize with nucleic acid from other enteroviruses (NPEVs) so as to prevent adequate positive hybridization with nucleic acids from a poliovirus.

The present invention further provides an isolated nucleic acid comprising the nucleotide sequence set forth in the Sequence Listing as SEQ ID NO:2. The consensus sequence set forth in SEQ ID NO:2 denotes the possible combinations of nucleotides that are found in SEQ ID NOS:13–20.

The present invention also provides an isolated nucleic acid that selectively hybridizes with a nucleic acid which is complementary to the nucleotide sequence set forth in the Sequence Listing as SEQ ID NO:2.

In a further embodiment, the present invention provides a primer for the detection of a poliovirus in a sample utilizing a nucleic acid amplification technique, comprising the nucleotide sequence set forth in the Sequence Listing as SEQ ID NO:1. The primer of the present invention can be utilized as a degenerate primer comprised of one or more of the possible combinations of nucleotide sequences set forth in the Sequence Listing as SEQ ID NOS:5–12. It is contemplated by the present invention that the nucleic acids described herein can be utilized in any of a number of nucleic acid detection techniques including, but not limited to polymerase chain reaction, isothermal DNA amplification, etc. Likewise, the nucleic acid set forth in SEQ ID NO:1 can be used as a probe for detecting or capturing a nucleic acid which hybridizes with the nucleic acid of SEQ ID NO:1.

The present invention also provides a primer for the detection of a poliovirus in a sample utilizing a nucleic acid amplification technique, comprising the nucleotide sequence set forth in the Sequence Listing as SEQ ID NO:2. The primer set forth in SEQ ID NO:2 can be utilized as a degenerate primer comprised of one or more of the possible combinations of nucleotide sequences set forth in the Sequence Listing as SEQ ID NOS:13–20. Similarly, the nucleic acid set forth in SEQ ID NO:2 can be used as a probe for detecting or capturing a nucleic acid which hybridizes with the nucleic acid of SEQ ID NO:2.

It is also contemplated by the present invention that any of the primers or probes described herein can be labeled or tagged for use in e.g., chemiluminescence or fluorescent detection systems.

In a further embodiment, the present invention provides a method for detecting the presence or absence of a poliovirus in a sample containing nucleic acids comprising the steps of:

a) amplifying the nucleic acids from the sample with a primer pair comprised of a primer comprising the nucleotide sequence set forth in the Sequence Listing as SEQ ID NO:1 and a suitable upstream primer;

b) determining the presence or absence of a nucleic acid from poliovirus, thereby detecting the presence or absence of poliovirus in the sample. As used herein, a "suitable upstream primer" for use with the primer comprising the nucleotide sequence set forth in the Sequence Listing as SEQ ID NO:1 is any of the possible primers which can be designed from known sequences for the VP1 gene located upstream (i.e., 5') of position number 2914 following the numbering system of Kew et al. (1990a). Examples of a suitable upstream primer include, but are not limited to the Panpv 2S and Panpv 13S primers described herein.

In a presently preferred embodiment, the invention provides a method for detecting the presence or absence of a poliovirus in a sample containing nucleic acids comprising the steps of:

a) amplifying the nucleic acids from the sample with a primer pair comprised of a first primer comprising the nucleotide sequence set forth in the Sequence Listing as SEQ ID NO:1 and a second primer comprising the nucleotide sequence set forth in the Sequence Listing as SEQ ID NO:2;

b) determining the presence or absence of a nucleic acid from poliovirus, thereby detecting the presence or absence of poliovirus in the sample.

In particular, the invention provides a method for detecting the presence or absence of a poliovirus in a sample containing nucleic acids utilizing polymerase chain reaction (PCR) amplification. An example of stringency conditions for in vitro PCR amplification with primers comprised of the nucleotide sequences set forth in SEQ ID NO:1 and SEQ ID NO:2 is set forth in Example 1.

Also contemplated by the present invention is a kit for detecting a nucleic acid of a poliovirus by nucleic acid amplification comprising a primer comprised of the nucleotide sequence set forth in the Sequence Listing as SEQ ID NO:1 and a suitable upstream primer. In one embodiment the invention provides a kit for detecting a nucleic acid of a poliovirus by nucleic acid amplification comprising a primer comprised of the nucleotide sequence set forth in the Sequence Listing as SEQ ID NO:1 and a primer comprising the nucleotide sequence set forth in the Sequence Listing as SEQ ID NO:2.

The present invention provides isolated synthetic nucleic acids comprising the nucleotide sequences set forth in the Sequence Listing as SEQ ID NO:22 through SEQ ID NO:28.

The present invention also provides isolated nucleic acids which selectively hybridize with nucleic acids which are complementary to the nucleotide sequences set forth in the Sequence Listing as SEQ ID NO:22 through SEQ ID NO:28. When used to refer to nucleic acids which selectively hybridize to nucleic acids which are complementary to the nucleotide sequences set forth in SEQ ID NOS:22–28, "selectively hybridizing" means that the synthetic nucleic acids derived from a particular poliovirus serotype do not hybridize with sequences from any other poliovirus serotype so as to prevent adequate positive hybridization with nucleic acid from the poliovirus serotype from which the synthetic nucleic acids were derived, i.e., the synthetic nucleic acid does not hybridize with more that one serotype of poliovirus so as to prevent adequate identification of that specific serotype of the virus.

In a further embodiment, the present invention provides degenerate primers for the detection of a specific serotype of poliovirus in a sample utilizing a nucleic acid amplification technique, comprised of the nucleotide sequences set forth in the Sequence Listing as SEQ ID NO:22 through SEQ ID NO:28.

It is contemplated by the present invention that the nucleic acids described herein can be utilized in any of a number of nucleic acid detection techniques including, but not limited to polymerase chain reaction, isothermal DNA amplification, liquid hybridization, etc. Likewise, the nucleic acid set forth in SEQ ID NO:22 through SEQ ID NO:28 can be used as probes for detecting or capturing a nucleic acid which hybridizes with the nucleic acid of SEQ ID NO:22 through SEQ ID NO:28.

It is also contemplated by the present invention that any of the primers or probes described herein can be labeled or tagged for use in e.g., chemiluminescence or fluorescent detection systems.

In a further embodiment, the present invention provides a method for detecting the presence or absence of poliovirus serotype 1 in a sample containing nucleic acids comprising the steps of:

a) amplifying the nucleic acids from the sample with a primer pair comprised of a first primer comprising the nucleotide sequence set forth in the Sequence Listing as SEQ ID NO:23 and a second primer comprising the nucleotide sequence set forth in the Sequence Listing as SEQ ID NO:22;

b) determining the presence or absence of a nucleic acid from poliovirus serotype 1, thereby detecting the presence or absence of poliovirus serotype 1 in the sample.

In another embodiment, the invention provides a method for detecting the presence or absence of poliovirus serotype 2 in a sample containing nucleic acids comprising the steps of:

a) amplifying the nucleic acids from the sample with a primer pair comprised of a first primer comprising the nucleotide sequence set forth in the Sequence Listing as SEQ ID NO:25 and a second primer comprising the nucleotide sequence set forth in the Sequence Listing as SEQ ID NO:24;

b) determining the presence or absence of a nucleic acid from poliovirus serotype 2, thereby detecting the presence or absence of poliovirus serotype 2 in the sample.

In another embodiment, the invention provides a method for detecting the presence or absence of poliovirus serotype 3 in a sample containing nucleic acids comprising the steps of:

a) amplifying the nucleic acids from the sample with a primer pair comprised of a first primer comprising the nucleotide sequence set forth in the Sequence Listing as SEQ ID NO:27 and a second primer comprising the nucleotide sequence set forth in the Sequence Listing as SEQ ID NO:26;

b) determining the presence or absence of a nucleic acid from poliovirus serotype 3, thereby detecting the presence or absence of poliovirus serotype 3 in the sample.

An example of the stringency conditions for in vitro PCR amplification of serotype-specific polioviral nucleic acids in the above methods utilizing primers comprised of the nucleotide sequences set forth in SEQ ID NOS:22–28 is set forth in Example 2.

In another embodiment, the invention provides a method for detecting the presence or absence of poliovirus serotype 3 in a sample containing nucleic acids comprising the steps of:

a) amplifying the nucleic acids from the sample with a primer pair comprised of a first primer comprising the nucleotide sequence set forth in the Sequence Listing as SEQ ID NO:28 and a primer comprising the nucleotide sequence set forth in the Sequence Listing as SEQ ID NO:26;

b) determining the presence or absence of a nucleic acid from poliovirus serotype 3, thereby detecting the presence or absence of poliovirus serotype 3 in the sample.

Also contemplated by the present invention is a kit for detecting a nucleic acid of poliovirus serotype 1 by nucleic acid amplification comprising a primer comprised of the nucleotide sequence set forth in the Sequence Listing as SEQ ID NO:22 and a primer comprised of the nucleotide sequence as set forth in the Sequence Listing as SEQ ID NO:23.

In one embodiment the invention contemplates a kit for detecting a nucleic acid of poliovirus serotype 2 by nucleic acid amplification comprising a primer comprised of the nucleotide sequence set forth in the Sequence Listing as SEQ ID NO:24 and a primer comprising the nucleotide sequence set forth in the Sequence Listing as SEQ ID NO:25.

In another embodiment the invention contemplates a kit for detecting a nucleic acid of poliovirus serotype 3 by nucleic acid amplification comprising a primer comprised of the nucleotide sequence set forth in the Sequence Listing as SEQ ID NO:26 and a primer comprising the nucleotide sequence set forth in the Sequence Listing as SEQ ID NO:27.

In yet another embodiment the invention contemplates a kit for detecting a nucleic acid of a poliovirus by nucleic acid amplification comprising a primer comprised of the nucleotide sequence set forth in the Sequence Listing as SEQ ID NO:26 and a primer comprising the nucleotide sequence set forth in the Sequence Listing as SEQ ID NO:28.

The present invention also provides isolated nucleic acids that are capable of selectively hybridizing with nucleic acids that are complementary to nucleic acids comprising the nucleotide sequences set forth in the Sequence Listing as SEQ ID NO:22 through SEQ ID NO:28. Likewise, the present invention provides isolated nucleic acids that are capable of selectively hybridizing with nucleic acids that are complementary to nucleotide sequences set forth in the Sequence Listing as SEQ ID NOS: 1 and 2. It is contemplated that modification (e.g., single nucleotide substitutions, additions, or deletions) to the synthetic nucleic acids set forth in the Sequence Listing can be made which will not prevent these synthetic nucleic acids from annealing to the conserved target polioviral sequences from which they were derived. Such modified nucleic acids are still within the invention if they selectively hybridize with the sequence necessary for hybridization, i.e., the sequence complementary to the primer sequence set forth.

Computer programs are readily available to the skilled artisan which can be used to compare the complementary modified sequences to previously published sequences of poliovirus to select the most appropriate sequences for amplification and hybridization. The specificity of these sequences for the different poliovirus serotypes can be determined by conducting a computerized comparison with known sequences catalogued in GENBANK, a computerized database, using the computer programs Word Search or FASTA of the Genetics Computer Group (Madison, Wis.), which search the catalogued nucleotide sequences for similarities to the nucleic acid in question.

In particular, nucleic acid that selectively hybridizes with (or selectively amplifies) the nucleic acids which are complementary to the nucleotide sequences set forth in SEQ ID NOS: 1, 2 and 22–28 under stringent conditions and has at least 70% complementarity with the segment of the complementary nucleic acid of SEQ ID NOS:1, 2 and 22–28 to which it hybridizes is provided. As used herein to describe nucleic acids, the term "selectively hybridizes" excludes the occasional randomly hybridizing nucleic acids and thus has the same meaning as "specific amplification".

The selectively hybridizing nucleic acids of the invention can have, for example, at least 70%, 80%, 85%, 90%, 95%, 97%, 98% and 99% homology with SEQ ID NOS:1, 2 and 22–28 or complementarity with the segment of the sequence to which it hybridizes. If used as primers, the invention provides compositions including at least two nucleic acids which selectively hybridize with different regions so as to amplify a desired region. For example, the nucleic acids identified by SEQ ID NO:1 and 2 selectively hybridize with a conserved region of the poliovirus VP1 genome. Likewise, the nucleic acids identified by SEQ ID NOS:22–28 selectively hybridize with a specific serotype of poliovirus as set forth herein. Depending on the length of the probe or primer, a target region can range between 70% complementary bases and full complementarity and still hybridize under stringent conditions. For example, for the purpose of diagnosing the presence of a specific poliovirus serotype, the degree of complementarity between the hybridizing nucleic acid (probe or primer) and the sequence to which it hybridizes is at least enough to exclude hybridization with a nucleic acid from another serotype. Thus, a nucleic acid that selectively hybridizes with a specific poliovirus serotype sequence (as set forth in SEQ ID NOS:22–28) will not selectively hybridize under stringent conditions with a nucleic acid of a segment of another serotype, and vice versa. Likewise a nucleic acid which selectively hybridizes with a nucleic acid complementary to a nucleic acid identified by SEQ ID NOS:1 and 2 will not selectively hybridize under stringent conditions with nucleic acid from another enterovirus. Nucleic acids which selectively hybridize with complementary nucleic acids to the nucleic acids identified by SEQ ID NOS:22–28 will selectively hybridize under stringent conditions to nucleic acid from a single serotype of poliovirus so as to positively identify the amplified serotype.

"Stringent conditions" refers to the hybridization conditions used in a hybridization protocol, for example, RNA/RNA hybridization, as in the genogrouping method. In general, these conditions should be a combination of temperature and salt concentration for washing, chosen so that the denaturation temperature is approximately 5–20° C. below the calculated $T_m$ (melting/denaturation temperature) of the hybrid under study. The temperature and salt conditions are readily determined empirically in preliminary experiments in which samples of reference RNA are hybridized to the primer nucleic acid of interest and then amplified under conditions of different stringencies. The stringency conditions are readily tested and the parameters altered are readily apparent to one skilled in the art. For example, $MgCl_2$ concentrations used in the reaction buffer can be altered to increase the specificity with which the primer binds to the template, but the concentration range of this compound used in hybridization reactions is narrow, and therefore, the proper stringency level is easily determined. For example, hybridizations with oligonucleotide probes 18 nucleotides in length can be done at 5–10° C. below the estimated $T_m$ in 6X SSPE, then washed at the same temperature in 2X SSPE (see, e.g., Sambrook et al., *Molecular Cloning: A Laboratory Manual*, 2nd Ed., Cold Spring Harbor Laboratory, Cold Spring Harbor, N.Y. (1987)). The $T_m$ of such an oligonucleotide can be estimated by allowing 2° C. for each A or T nucleotide, 4° C. for each G or C, and about 2° C. for each deoxyinosine. Temperature and salt conditions can be adjusted from the conditions set forth in Example 1 and Example 2. In an 18 nucleotide primer, for example, stating a suitable range for the $T_m$ is between about 47–50° C. with starting salt concentrations of between about 100–200 mM and modified accordingly by preliminary experiments. $T_m$ values can also be calculated for a variety of conditions utilizing commercially available computer software (e.g., OLIGO™).

The oligonucleotides comprising SEQ ID NOS:1, 2 and 22–28, if used as primers in amplification of template DNA or reverse transcription of viral RNA, or for use as a probe in a hybridization and detection assay can vary in length. These oligonucleotides are typically between 10 and 100 nucleotides in length, especially 12 and 30 nucleotides in length with a preferable range of 15–25 nucleotides. Thus, the sequences on the terminal ends of the primers set forth in the sequence listing are preferably limited but, if included, should not inerfere with selective binding. One skilled in the art, however, will readily appreciate that there is no standard length for optimal polymerase chain reaction amplification, reverse transcription, or hybridization, but that an optimal length for a particular application is readily determined. (PCR Technology, Principles and Applications for DNA Amplification, H. A. Erlich, Ed. (1989)). Several computer software programs are available to facilitate primer design. (Lowe, T., Sharefkin, J., Yang, S. Q., and Dieffenbach, C. W. A. "Computer program for selection of oligonucleotide primers for polymerase chain reactions." Nucl. Acids. Res. 18:1757–1761 (1991) and RT-PCR, Methods and Applications Book 1. Clontech Laboratories, Inc. (1991)).

A nucleic acid specific for each serotype of poliovirus can be detected utilizing a nucleic acid amplification technique, such as polymerase chain reaction (PCR) as taught in the examples described herein. Alternatively, the nucleic acid is detected utilizing direct hybridization or by utilizing a restriction fragment length polymorphism. Additionally, the present invention contemplates a method of detecting the presence of all poliovirus genotypes to the exclusion of nonpolio enteroviruses. PCR primers which hybridize only with nucleic acids specific for a target sequence (e.g., SEQ ID NO:3) of the poliovirus can be utilized. The presence of amplification indicates the presence of the virus. Alternatively, the poliovirus can be detected by directly hybridizing the target sequence with a nucleic acid probe selective for the specific target sequence of the poliovirus.

Polymerase chain reaction PCR) and RT/PCR are examples of techniques that amplify specific nucleic acid sequences with remarkable efficiency. Repeated cycles of denaturation, primer annealing and extension carried out with a polymerase, e.g., the heat stable enzyme Taq polymerase, leads to exponential increases in the concentration of desired nucleic acid sequences. Given a knowledge of the appropriate target nucleic acid sequence of the poliovirus as provided by the present invention, synthetic oligonucleotides can be prepared which are complementary to all of the possible sequences in the poliovirus of interest. Each oligonucleotide primer species is complementary to one of the possible poliovirus specific degenerate sequences of interest. The nucleic acid can be denatured at high temperatures (e.g., 95° C.) and then reannealed in the presence of a large molar excess of the oligonucleotides. The oligonucleotides, oriented with their 3' ends pointing towards each other, hybridize to opposite strands of the target sequence and prime enzymatic extension along the nucleic acid template in the presence of the four deoxyribonucleotide triphosphates. The end product is then denatured again for another cycle. After this three-step cycle has been repeated several times, amplification of a nucleic acid segment by more than one million-fold can be achieved. The resulting nucleic acid may then be directly detected by any of a number of methods well known in the art (for example, Southern blotting using poliovirus specific probes as described above).

Better amplification is obtained when both primers are the same length and with roughly the same nucleotide composition. Denaturation of strands usually takes place at about 94° C. and extension from the primers is usually at about 60° C. The annealing temperature varies according to the sequence under investigation, but usually about 42° C. Examples of reaction times are: 20 mins denaturing; 35 cycles-of 2 min, 1 min, and 1 min for annealing, extension and denaturation, respectively; and finally, a 5 min extension step.

Modifications to the nucleic acids of the invention are also contemplated as long as the essential structure and function (i.e., annealing to the target polioviral nucleic acid) of the polypeptide encoded by the nucleic acids is maintained. Likewise, fragments used as primers or probes can have substitutions so long as enough complementary bases exist for selective hybridization and amplification as set forth herein (see also, Kunkel et al., *Methods Enymol.* 154:367 (1987)).

The present invention is more particularly described in the following examples which are intended as illustrative only since numerous modifications and variations therein will be apparent to those skilled in the art.

EXAMPLE 1

Poliovirus specific primers

Viruses:

Poliovirus isolates (Tables 1 and 2) have been previously characterized by neutralization with hyperimmune equine sera and partial genomic sequencing (Rico-Hesse et al., 1987; Kew et al 1990a; De et al., in preparation). Vaccine-related strains were also positively identified by PCR using the Sabin strain-specific primer pairs (Yang et al., 1991). Fourteen human nonpolio enteroviruses were identified by confirmation of serotype with monotypic neutralizing polyclonal antibodies. Viruses were propagated in HeLa or RD monolayers to produce high-titer inoculation stocks.

TABLE 1

Vaccine-Related Poliovirus Genotypes Detected by Pan-Polio PCR

Type 1

| | | | |
|---|---|---|---|
| 0584/GUT91 | 0246/GUT90 | 9825/USA89 | 9703/ELS89 |
| 9360/VEN89 | 9240/HON89 | 2800/H0N91 | 8315/MEX88 |
| 6258/MOR85 | 5498/USA84 | | |

Type 2

| | | | |
|---|---|---|---|
| 0636/ELS91 | 0042/ELS90 | 9897/GUT90 | 0078/PER89 |
| 9818/PER89 | 9519/USA89 | 8370/PER88 | 8018/GUT87 |
| 7653/SOA89 | 7170/MEX86 | 6700/HON86 | 7837/PER84 |
| 6886/GUT83 | | | |

Type 3

| | | | |
|---|---|---|---|
| 1063/USA91 | 0644/HON91 | 0642/ELS91 | 0405/GUT90 |
| 0040/ELS90 | 0131/MEX89 | 0044/GUT89 | 9896/GUT89 |
| 9442/NIC89 | 9441/GUT89 | 8774/TRT88 | 1339/CHN89 |
| 8239/GUT87 | 6880/COL86 | | |

TABLE 2

Wild Poliovirus Genotypes Detected by Pan-Polio PCR

Type 1

| | | | |
|---|---|---|---|
| 0006/CHN89 | 0109/CHN89 | 0032/CHN91 | 0124/CHN91 |
| 0285/INO86 | 0289/POR87 | 0427/SSR91 | 0440/SSR90 |
| 0467/COL89 | 0941/SRL87 | 0955/SRL88 | 1184/ROM91 |
| 1187/ROM91 | 1338/CHN89 | 1607/SOA88 | 2609/ETH91 |
| 2611/PAK90 | 2662/COL87 | 2758/SVN89 | 2786/VTN90 |
| 2854/HON91 | 3638/CHN85 | 3643/CHN91 | 3647/CHN91 |
| 3677/CYP92 | 3706/MAA92 | 3907/PHL91 | 3940/THA92 |
| 6224/ZIM85 | 6536/NEP86 | 6700/TUR90 | 6701/TUR90 |
| 6750/SEN86 | 7054/IND86 | 7169/BUL91 | 7362/PAK91 |
| 7377/BOL86 | 8223/GUT87 | 8425/ISR88 | 8644/IND91 |
| 8645/IND92 | 8649/IND91 | 8771/OMA88 | 9366/SAA89 |
| 9475/ZAI89 | 05145/UZB88 | 07470/TOG92 | 09323/MOG91 |
| 11231/EGY91 | 11236/EGY91 | 11267/EGY91 | 11270/EGY91 |
| 15949/FRA89 | 16834/TUR90 | 16838/TUR90 | 18641/PAK91 |
| 18655/PAK91 | | | |

Type 2

| | | | |
|---|---|---|---|
| 0290/TUR73 | 0291/TUR73 | 0295/ISR78 | 0297/KUW78 |
| 0298/EGY79 | 0302/YUG81 | 0305/IRA71 | 1155/ALB91 |
| 1534/IND82 | 2613/PAK89 | 2710/KEN71 | 6876/COL86 |
| 7079/IND82 | 7354/PAK91 | 8650/IND91 | 8654/IND91 |
| 05144/UZB88 | 11263/EGY91 | 18637/PAK91 | 18638/PAK91 |

Type 3

| | | | |
|---|---|---|---|
| 0314/ROM80 | 0380/MEX90 | 0426/SSR90 | 0672/OMA91 |
| 2615/MOL90 | 2619/MOL90 | 2723/TUR90 | 2728/ARM90 |
| 2731/URZ89 | 4075/ARM90 | 6184/FIN84 | 7095/IND86 |
| 7350/PAK91 | 7377/BOL86 | 8178/VEN87 | 8668/IND91 |
| 8670/IND91 | 9035/BRA88 | 9259/TUN88 | 05141/UZB88 |
| 05142/UZB88 | 11246/EGY91 | 11252/EGY91 | 11257/EGY91 |
| 15952/FRA90 | 16837/TUR90 | 18643/PAK91 | 18653/PAK91 |

Oligonucleotide synthesis:

Synthetic oligodeoxynucleotides were prepared, purified, and analyzed as described (Yang et al., 1991). The degenerate primers used for amplifying poliovirus are;

Panpv 1A (A:2915–2934) 5'-TTIAIGC(AG)TGICC(AG)TT(AG)TT-3' (SEQ ID NO:1)

Panpv 2S (S:2852 2871) 5'-TTCAC(AC)TAITCIAG(N)TTTGA-3' (SEQ ID NO:21)

Panpv 13S (S:2852–2871) 5'-TTCAC(AC)TAITCI(AC)GITT(TC)GA-3' (SEQ ID NO:2)

The numbers in parentheses indicate the genomic intervals matching the primers (A=antigenome polarity primer; S=sense or genome polarity primer; following the numbering system of Kew et al. (1990a). Primer Panpv 1A as used herein refers to the consensus sequence set forth in the sequence listing as SEQ ID NO:1. The eight possible primer species for the consensus sequence SEQ ID NO:1 are set forth in the Sequence Listing as SEQ ID NOS:5–12. Primer Panpv 13S as used herein refers to the consensus sequence set forth in the Sequence Listing as SEQ ID NO:2. The eight possible primer species for the consensus sequence SEQ ID NO:2 are set forth in the Sequence Listing as SEQ ID NOS:13–20. Primer Panpv 2S as used herein refers to the consensus sequence set forth in the Sequence Listing as SEQ ID NO:21.

PCR amplification and analysis:

In vitro amplification by PCR was performed as described previously (Yang et al., 1992). Amplification reactions were carried out in 50 µl reaction mixtures containing 1 µl of each individual virus tissue culture lysate in 50 mM Tris-HCl (pH 8.3), 70 mM KCl, 5 mM $MgCl_2$, 10 mM dithiothreitol, 10 pmol of each primer, 200 µM each of dATP, dCTP, dGTP, dTTP (Pharmacia), 0.5% NP-40, 10 U placenta ribonuclease inhibitor (Boehringer Mannheim Biochemicals, Indianapolis, Ind.), 2.5 U AMV reverse transcriptase (Boehringer Mannheim), and 2.5 U of Taq DNA polymerase (Perkin Elmer-Cetus, Norwalk, Conn.). The reaction mixtures were prepared, excluding the ribonuclease inhibitor, AMV reverse transcriptase, and Taq DNA polymerase, overlaid with mineral oil, heated for 5 min at 95° C. to release the virion RNA and chilled on ice. The enzymes were then added and the samples incubated at 42° C. for 30 min before 30 cycles of programmed amplification (denaturation:94° C., 1 min; annealing:42° C., 1 min; extension:60° C., 1 min) in a DNA thermal cycler (Perkin Elmer-Cetus). Conditions for polyacrylamide gel electrophoresis, and detection of amplified products by ethidium bromide staining were as described (Yang et al., 1991).

Selection of primer binding sites:

The amino acid alignment in the capsid protein region (Palmenberg, 1989) of a wide variety of picornaviruses was used to find poliovirus amino acid residues that were near residues suspected to be involved in receptor attachment/recognition and conserved among only picornaviruses. A 7 amino acid sequence in VP1 (NNGHALN, as set forth in the Sequence Listing as SEQ ID NO:3) that was unique to only polioviruses was chosen as a possible PCR primer site. A degenerate PCR primer (anti-sense; designated as Panpv 1A) was designed using this sequence information as well as possible nucleotide incorporation at the first and third codon positions due to codon degeneracy. Deoxyinosine residues were used in those positions where 3 or 4 different nucleotides were possible. This was done to keep the number of possible primer species at a minimum. Since there are 8 possible species of Panpv 1A (SEQ ID NOS:5–12), a concentration of 80 picomoles was used per reaction (10 pM/primer species). Similarly, another 7 amino acid (FTYSRFD, as set forth in the Sequence Listing as SEQ ID NO:4) sequence was located upstream from Panpv 1A and chosen as the sense PCR primer site (designated as Panpv 2S). This PCR primer set yields an 83 bp PCR product. We generally use primer pairs that are closely spaced (<250 nucleotides) along the template because AMV reverse transcriptase has relatively low processivity (Berger et al., 1983). Diagnostic sensitivities are generally improved by reducing the lengths of the cDNA transcripts required to initiate the chain reactions.

Detection of vaccine-related polioviruses:

The Panpv 1A/2S primer pair was first tested against different vaccine-related poliovirus genotypes since they would have the least amount of nucleotide sequence heterogeneity. One microliter of each infected tissue culture lysate was amplified in an RT/PCR reaction mixture. After 30 amplification cycles, DNA products were separated by electrophoresis on 12% polyacrylamide gels and visualized the ethidium bromide staining. A single 83 bp product was seen from all samples. The remaining vaccine-related isolates also yielded this same 83 bp product. A wide range of genotypes from around the world and representing all three serotypes was also tested. All of the isolates tested positive (Table 1).

Detection of wild polioviruses:

Poliovirus genomes evolve rapidly during replication in humans. However, the 7 amino acid sequences set forth in SEQ ID NO:3 were found to be absolutely conserved in the 23 complete VP1 nucleotide sequences presently in the Centers for Disease Control and Prevention (CDC) data base. An 83 bp PCR product was found when 13 wild type 1 poliovirus isolates were tested with the Panpv 1A/2S primer set. Subsequently, all 120 poliovirus isolates (Table 2) were found to be positive. This suggests that the NNGHALN amino acid sequence is conserved among all polioviruses. However, in six isolates a weak PCR product was detected. This was thought to be a result of poor primer homology due to the upstream Panpv 2S primer. Further analysis found that in some instances the minus 3 and minus 8 positions from the 3'-terminus of the 2S primer do not correctly match the virus sequence (for example isolate 9288/MEXVP1 has a C at positions minus 3 and minus 8). Proper annealing at the 3' end of the primer is known to be very important to the fidelity of Taq polymerase in extending the sequence. Panpv 2S was re-designed to contain a T or C at the minus 3 position and an A or C at the minus 8 position to see if this would increase the yield of the PCR product (since the nucleotide sequences for these isolates was unknown). A deoxyinosine residue was also introduced at the minus 6 position to reduce the number of primer species. This new primer, Panpv 13 S was used along with Panpv 1A to amplify the isolates which gave the weakest priming. The results showed a stronger PCR product when this new primer was used, as compared to the original Panpv 2S primer. This indicates that the weaker PCR product found with a few virus isolates is due to poor annealing of the Panpv 2S primer and not to weak annealing of Panpv 1A.

Specificity:

The primary need for developing poliovirus specific PCR is to rapidly distinguish poliovirus cases of acute flaccid paralysis (AFP) from NPEV cases of AFP. This is becoming increasingly important in the surveillance of AFP cases in those areas of the world that have essentially eliminated wild poliovirus. When the Panpv 1A/2S primer pair was tested against a wide range of nonpoliovirus enteroviruses, no amplification products were detected. These data supported our early hypothesis that the NNGHALN amino acid sequence in VP1 is unique among all polioviruses. To prove that each isolate tested did indeed contain viable virus, these same isolates were tested with an enterovirus specific primer pair (EV/PCR-1 & EV PCR-2). This primer pair recognizes highly conserved nucleotide sequences in the 5' noncoding region in a wide range of enteroviruses (Yang et al., 1992). The expected 114 bp PCR product of the enterovirus primer pair was identified in all of the isolates tested. This indicates that the Panpv 1A/2S primer pair is specific for polioviruses and does not recognize other enteroviruses.

Detection of poliovirus in an isolate typed as NPEV:

Virus isolates are presently typed as NPEV by their ability to replicate in the presence of neutralizing antisera specific to polioviruses. However, low titers of poliovirus can be masked by the presence of higher NPEV titers. Such a case was suspected due to uncharacteristic growth in tissue culture during typing. Two suspected poliovirus cases originally typed as NPEV were tested with the Panpv 1A/2S primer set. The 83 bp PCR product characteristic of the primer pair was detected and clearly indicated the presence of poliovirus. A serotype 1 poliovirus was eventually isolated from this sample. This shows that the pan-poliovirus PCR primer set would be very useful in rapidly distinguishing poliovirus from NPEV in samples containing both virus types.

EXAMPLE 2

Serotype specific poliovirus primers

Viruses:

Poliovirus isolates (Tables 3 and 4) have been previously characterized by neutralization with hyperimmune equine sera, partial genomic sequencing and probe hybridization (Rico-Hesse et al., 1987; Kew et al., 1990a; De et al., manuscript in preparation). Vaccine-related strains were also positively identified by PCR using the Sabin strain-specific primer pairs (Yang et al., 1991). Viruses were propagated in HeLa or RD monolayers to produce high-titer inoculation stocks.

TABLE 3

Vaccine-Related Poliovirus Tested With Serotype-Specific PCR

| Type 1 | | | |
|---|---|---|---|
| 0584/GUT91 | 0246/GUT90 | 9825/USA89 | 9703/ELS89 |
| 9360/VEN89 | 9240/HON89 | 2800/H0N91 | 8315/MEX88 |
| 8284/HON88 | 8221/GUT87 | 6529/CHI86 | 6440/ARG85 |
| 6258/MOR85 | 5498/USA84 | | |

| Type 2 | | | |
|---|---|---|---|
| 0636/ELS91 | 0042/ELS90 | 9897/GUT90 | 0078/PER89 |
| 9818/PER89 | 9519/USA89 | 8370/PER88 | 8018/GUT87 |
| 7653/SOA86 | 7170/MEX86 | 6700/HON86 | 7837/PER84 |
| 6886/GUT83 | | | |

| Type 3 | | | |
|---|---|---|---|
| 1063/USA91 | 0644/HON91 | 0642/ELS91 | 0405/GUT90 |
| 0040/ELS90 | 0131/MEX89 | 0044/GUT89 | 9896/GUT89 |
| 9442/NIC89 | 9441/GUT89 | 8774/TRT88 | 1339/CHN89 |
| 8239/GUT87 | 6880/COL86 | | |

TABLE 4

Wild Poliovirus Tested With Serotype-Specific PCR

| Type 1 | | | |
|---|---|---|---|
| 0006/CHN89 | 0109/CHN86 | 0032/CHN91 | 0124/CHN91 |
| 0285/INO86 | 0289/POR87 | 0427/SSR91 | 0440/SSR90 |
| 0467/COL89 | 0941/SRL87 | 0955/SRL88 | 1184/ROM91 |
| 1187/ROM91 | 1338/CHN89 | 1607/SOA88 | 2609/ETH91 |
| 2611/PAK90 | 2662/COL87 | 2758/SVN89 | 2786/VTN90 |
| 2854/HON91 | 3638/CHN85 | 3643/CHN91 | 3647/CHN91 |
| 3677/CYP92 | 3706/MAA92 | 3907/PHL91 | 3940/THA92 |
| 6224/ZIM85 | 6536/NEP86 | 6700/TUR90 | 6701/TUR90 |
| 6750/SEN86 | 7054/IND86 | 7169/BUL91 | 7362/PAK91 |
| 7377/BOL86 | 8223/GUT87 | 8425/ISR88 | 8644/IND91 |
| 8645/IND92 | 8649/IND91 | 8771/OMA88 | 9366/SAA89 |
| 9475/ZAI89 | 05145/UZB88 | 07470/TOG92 | 09323/MOG91 |
| 11231/EGY91 | 11236/EGY91 | 11267/EGY91 | 11270/EGY91 |
| 15949/FRA89 | 16834/TUR90 | 16838/TUR90 | 18641/PAK91 |
| 18655/PAK91 | | | |

| Type 2 | | | |
|---|---|---|---|
| 0290/TUR73 | 0291/TUR73 | 0295/ISR78 | 0297/KUW78 |
| 0298/EGY79 | 0302/YUG81 | 0305/IRA71 | 1155/ALB91 |
| 1534/IND82 | 2613/PAK89 | 2710/KEN71 | 6876/COL86 |

TABLE 4-continued

Wild Poliovirus Tested With Serotype-Specific PCR

| 7079/IND82 | 3833/PAK91 | 8650/IND91 | 8654/IND91 |
|---|---|---|---|
| 05144/UZB88 | 3636/PAK91 | 3848/PAK91 | 18638/PAK91 |

Type 3

| 0314/ROM80 | 0380/MEX90 | 0426/SSR90 | 0672/OMA91 |
|---|---|---|---|
| 2615/MOL90 | 2619/MOL90 | 2723/TUR90 | 2728/ARM90 |
| 2731/URZ89 | 4075/ARM90 | 6184/FIN84 | 7095/IND86 |
| 7350/PAK91 | 7377/BOL86 | 8178/VEN87 | 8668/IND91 |
| 8670/IND91 | 9035/BRA88 | 9259/TUN88 | 05141/UZB88 |
| 05142/UZB88 | 11246/EGY91 | 11252/EGY91 | 11257/EGY91 |
| 15952/FRA90 | 16837/TUR90 | 18643/PAK91 | 18653/PAK91 |

Oligonucleotide synthesis:

Synthetic oligodeoxynucleotides were prepared, purified, and analyzed as described (Yang et al., 1991). The degenerate primers used for amplifying individual serotypes are:

Sero 2sP1  5'-TGCGIGA(TC)ACIACICA(TC)AT-3'
(2439–2457)
(SEQ ID NO:22)
Sero 2aP1  5'-CGIACIGT(AG)(TC)T(AG)TCIATCAT-3'
(2523–2504)
(SEQ ID NO:23)
Sero 4sP2  5'-GTII(GC)IGCTG(TC)AA(TC)GA(TC)TT-3'
(2420–2422)
(SEQ ID NO:24)
Sero 7aP2  5'-A(CT)ICC(TC)TCIACI(AG)CICC(TC)TC-3'
(2518–2499)
(SEQ ID NO:25)
Sero 8sP3  5'-AA(TC)CCITCIATITT(TC)TA(TC)AC-3'
(3008–3027)
(SEQ ID NO:26)
Sero 1aP3  5'-CCIAI(TC)TG(AG)TCATTI(TG)C(AG)TC-3'
(3147–3128)
(SEQ ID NO:27)
Sero 3aP3  5'-A(AG)IGCIC(TC)(TC)TGIGCIACITC-3'
(2498–2517)
(SEQ ID NO:28)

The numbers in parentheses indicate the genomic intervals matching the primers a=antigenome polarity primer; s=sense or genome polarity primer), following the umbering system of Kew et al., (1990a). Deoxyinosine residues are indicated by the letter I.

PCR amplification and analysis:

In vitro amplification by PCR was performed as described previously (Yang et al., 1991). Amplification reactions were carried out in 50 μl reaction mixtures containing 1 μl of each individual virus tissue culture lysate in 50 mM Tris-HCl (pH 8.3), 70 mM KCl, 5 mM MgCl$_2$, 10 mM dithiothreitol, 80 pmol of each degenerate primer, 200 μM each of dATP, dCTP, dGTP, dTTP (Pharmacia), 0.5% NP-40, 10 U placenta rib onuclease inhibitor (Boehringer Mannheim Biochemicals, Indianapolis, Ind.), 2.5 U AMV reverse transcriptase (Boehringer Mannheim), and 2.5 U of Taq DNA polymerase (Perkin Elmer-Cetus, Norwalk, Conn.). The reaction mixtures were prepared, excluding the ribonuclease inhibitor, AMV reverse transcriptase, and Taq DNA polymerase, overlaid with mineral oil, heated for 5 min at 95° C. to release the virion RNA and chilled on ice. The enzymes were then added and the samples incubated at 42° C. for 30 min before 30 cycles of programmed amplification (denaturation:94° C., 1 min; annealing:42° C., 1 min; extension:60° C., 1 min) in a DNA thermal cycler (Perkin Elmer-Cetus). Conditions for polyacrylamide gel electrophoresis, and detection of amplified products by ethidium bromide staining were as described (Yang et al., 1991).

Serotype-specific PCR primer design:

It was not known, prior to this invention, whether amino acid sequences in VP1 would show any conservation unique to each serotype. The complete poliovirus VP1 amino acid alignments in our database revealed several areas which contained amino acid sequences unique to a particular serotype. The greatest serotype-specific sequence conservation is near the 5' end of VP1. Specific sequences were found to be unique for a given serotype: MIDNTVR (a.a. 9–15 VP1, as set forth in the Sequence Listing as SEQ ID NO:29, primer 2aP1) sequence for serotype 1, EGVVEGV (a.a. 7–13 VP1, as set forth in the Sequence Listing as SEQ ID NO:30, primer 7aP2) for serotype 2, and EVAQGAL (a.a. 9–15 VP1, as set forth in the Sequence Listing as SEQ ID NO:31, primer 3aP3) for serotype 3. In addition, a serotype 3 conserved amino acid sequence (DANDQIG; a.a. 218–224 VP1, as set forth in the Sequence Listing as SEQ ID NO:32, primer 1aP3) was found closer to the 3' end of the VP1 gene in a region previously identified as poliovirus neutralization site 2a (Minor et al., 1986b). The PCR primer recognizing the serotype 3 specific site near the 3' end of VP1 (1aP3) was primarily used in serotyping since it was found that the serotype 3 specific primer near the 5' end of VP1 (3aP3) was less consistent due to the deoxyinosine residue at the 3rd position from the 3' end of the primer (data not shown). The presence of deoxyinosine residues near the 3' end of the primer is believed to result in lower discrimination between bases (3atzer et al., 1991; Case-Green and Southern, 1994) which could result in less consistent reverse transcription and subsequently, poor amplification. The appropriate upstream conserved amino acid sequences were also identified: LRD)TTHI (a.a. 225–231 VP3, as set forth in the Sequence Listing as SEQ ID NO:33, primer 2sP1) for serotype 1, VSACNDF (a.a. 214–220 VP3, as set forth in the Sequence Listing as SEQ ID NO:34, primer 4sP2) for serotype 2, and NPSIFYT (a.a. 180–186 VP1, as set forth in the Sequence Listing as SEQ ID NO:35, primer 8sP3) for serotype 3. Degenerate PCR primers were designed that recognize these conserved amino acid sequences and the anti-sense primers. The serotype-specific antisense PCR primers target unique amino acids only found in polioviruses. Therefore, these PCR primers do not amplify non-poliovirus enteroviruses (data not shown). This is especially important since, in many cases, polioviruses and non-polioviruses may be present in the same isolate.

Serotype specificity:

Tables 3 & 4 list the 40 vaccine-related and 100 wild type polioviruses which represent most of the major genotypes presently found in nature. All isolates were tested with each serotype-specific PCR primer pair. All serotype 1 isolates amplified with 2sP1/2aP1 yielded an 85 bp PCR product. No products of the correct size (i.e. 85 bp) were seen when the 2sP1/2aP1 primer pair was tested with isolates representing serotypes 2 and 3. All serotype 2 isolates yielded a 115 bp PCR product when analyzed with the serotype 2 specific primers 4sP2/7aP2. PCR analysis of serotypes 1 and 3 with this primer pair were all negative. One serotype 1 isolate (8425/ISR88) did yield the correct 115 bp serotype 2 product. This isolate was found to contain a mixture of wild type 1 and vaccine-related type 2, using Sabin 2-specific primers (data not shown). All serotype 3 isolates yielded a 140 bp PCR product when analyzed with the serotype 3 primer pair 8sP3/1aP3. PCR analysis of serotype 1 isolates and serotype 2 isolates were negative with the serotype 3 primers. All poliovirus isolates listed in Tables 3 & 4 gave the correct PCR product with their respective serotype-specific primers. None of the serotype-specific primers yielded false positive PCR products with other serotypes, except in those cases where mixtures of serotypes were discovered. The detection of mixed serotypes in isolates thought to contain only 1 serotype suggests that the use of neutralization inhibition tests by limiting dilutions for serotyping polioviruses is not as sensitive as PCR. Neutralization inhibition tests are especially troublesome when small amounts of poliovirus are present in isolates which contain large titers of non-poliovirus enteroviruses. This often results in poliovirus isolates being classified as nonpoliovirus enteroviruses due to the lack of virus neutralization in the presence of all three serotype-specific antisera. The level of sensitivity for detecting polioviruses from tissue culture isolates using our PCR conditions is in the range of 10 to 20 viral genomes (Yang et al., 1991). This PCR sensitivity, when applied to serotyping poliovirus isolates, will greatly increase our ability to correctly serotype isolates containing either mixtures of different poliovirus serotypes or mixtures of nonpolioviruses and poliovirus.

Detection of serotypes 1 & 3 in the same PCR reaction:

There are relatively few circulating wild type 2 poliovirus genotypes still found in nature and as a result, the majority of isolates tested in our lab are either serotype 1 or 3. This is because serotype 2 poliovirus is the first of the serotypes to be eliminated from a region that has an established vaccination program (Patriarca et al., 1988; Kew et al., 1990). Therefore, in order to quickly screen isolates sent to CDC that have been previously serotyped in other labs (CDC is one of the reference labs in the poliovirus eradication program), a mixture containing serotype 1 and 3 specific primers was prepared. This primer mix was tested against all three serotypes to determine whether any of the primers would interact with each other (i.e. primer dimers) and if their serotype specificity was maintained. Since the primer sites for serotype 1 are located on either side of the VP3/VP1 junction and the sites for serotype 3 are nearer the 3' end of VP1 (about 700 nucleotides downstream from the serotype 1 primer site), no competition for primer binding sites on the same RNA genome was expected (although the anti-sense primers are serotype-specific, the sense primers are capable of binding to the reverse transcribed cDNA genomes of both serotypes). Serotype 1 & 3 primer mix still detects either serotype 1 or serotype 3 specifically and does not yield false positive products with serotype 2. No discrepancies were found when all of the polioviruses listed in Tables 3 & 4 were tested with this mixed serotype-specific PCR primer set.

The ability to determine poliovirus serotypes by PCR will greatly increase the speed and accuracy of poliovirus serotyping. These molecular reagents should accelerate the successful achievement of global poliovirus eradication.

Throughout this application, various publications are referenced by author and year. The disclosures of these publications in their entireties are hereby incorporated by reference into this application in order to more fully describe the state of the art to which this invention pertains. A complete reference citation is provided below.

Although the present process has been described with reference to specific details of certain embodiments thereof, it is not intended that such details should be regarded as limitations upon the scope of the invention except as and to the extent that they are included in the accompanying claims.

REFERENCES

Abraham, R., Chonmaitree, T., McCombs, J., Prabhakar, B., Lo Verde, P. T. and Ogra, P. L. (1993). Rapid detection of poliovirus by reverse transcription and polymerase chain amplification: Application for differentiation between poliovirus and nonpoliovirus enteroviruses.

Balanant et al. (1991). The natural genomic variability of Poliovirus analyzed by a restriction fragment length polymorphism assay. Virology 184, 845–854.

Batzer, M. A., Carlton, J. E., and Deininger, P. L. (1991). Enhanced evolutionary PCR using oligonucleotides with inosine at the 3'-terminus. Nucleic Acids. Res. 19, 5081.

Blondel, B., Crainic, R., Fichot, O., Dufraisse, G., Candrea, A., Diamond, D., Girard, M., and Horaud, F. (1986). Mutations conferring resistance to neutralization with monoclonal antibodies in type 1 poliovirus can be located outside or inside the antibody binding site. J. Virol. 57, 81–90.

Case-Green, S. C. and Southern E. M. (1994). Studies on the base pairing properties of deoxyinosine by solid phase hybridisation to oligonucleotides. Nucleic Acids Res. 22(2), 131–136.

Chapman, N. M., Tracy, S., Gauntt, C. J. and Fortmueller, U. (1990). Molecular detection and identification of enteroviruses using enzymatic amplification and nucleic acid hybridization. J. Clin. Micr. 28, 843–850.

Chow, M., Yabrov, R., Bittle, J., Hogle, J. and Baltimore, D. (1985). Synthetic peptides from four seperate regions of the poliovirus type 1 capsid protein VP1 induce neutralizing antibodies. Proc. Natl. Acad. Sci. USA 82, 910–914.

De, L., Nottay, B., Yang, C. -F., Holloway, B. P., Pallansch, M., and Kew, O. (1994). Identification of vaccine-related polioviruses by molecular hybridization with specific RNA probes. Manuscript in preparation.

de Qaudros, C. A., Andurs, J. K., Olive, J. -M., da Silveira, C. M., Eikhoff, R. M., Carrasco, P., Fitzsimmons, J. W. and Pinheiro, F. P. (1991). Eradications of poliomyelitis: progress in the Americas. Pediatr. Inf. Dis. J. 10, 222–229.

Diamond, D. C., Jameson, B. A., Bonin, J., Kohara, M., Abe, S., Itoh, H., Komatsu, T., Arita, M., Kuge, S., Nomoto, A., Osterhaus, A. D. M. E., Crainic, R., and Wimmer, E. (1985). Antigenic variation and resistance to neutralization in poliovirus type 1. Science 229, 1090–1093.

Evans, D. M., Minor, P. D., Schild, G. C., and Almond, J. W. (1983). Critical role of an eight amino acid sequence of VP1 in neutralization of poliovirus type 3. Nature 304, 439–462.

Giranda, V. L., Chapman, M. S. and Rossman, M. G. (1990). Modeling of the human intercellular adhesion molecule-1, the human rhinovirus major group receptor.

Heinz, B. A., Shepard, D. A., Rueckert, R. R. (1989). Drug-resistant mutants of human rhinoviruses map to capsid regions involved in attachment. In: Europic 89. (abstr. no. G10).

Hogle, J. M., Chow, M., Filman, D. J. (1985). Three-dimensional structure of poliovirus at 2.9 A resolution. Science 229, 1358–1365.

Hyypia, T., Auvinen, P. and Maaronen, M. (1989). Polymerase chain reaction for human picomaviruses. J. Gen. Virol. 70, 3261–3268.

Ketterlinus, R., Wiegers, K. and Dernick, R. (1993). Revertants of poliovirus escape mutants: New insights into antigenic structures. Virol. 192, 525–533.

Kew, O. M. and Nottay, B. K. (1984). Evolution of the oral poliovaccine strains in humans occurs by both mutation and intramolecular recombination. In: R. Chanock and R. Lerner (Eds.), Modern approaches to vaccines, pp. 357–362. Cold Spring Harbor Laboratory, Cold Spring Harbor, N.Y.

Kew, O. M., Nottay, B. K., Rico-Hesses, R. R. and Pallansch, M. A. (1990a). Molecular epidemiology of wild poliovirus transmission. In: E. Kurstak, R. G., Marusyk, F. A., Murphy and M. H. V. Van Regenmortel (Eds.), Applied virology research, Vol. 2, pp. 99–221. Plenum Press, New York.

Kew, O. M., Pallansch, M. A., Nottay, B. K., Rico-Hesse, R. R., De, L. and Yang, C. -F. (1990b). Genotypic relationships among wild polioviruses from different regions of the world. In: M. A. Brinton and F. X. Heinz (Eds.), New Aspects of Positive-Strand RNA Viruses. pp. 357–365. American Society for Microbiology, Washington, DC.

King, A. M. Q. (1988). Preferred sites of recombination in poliovirus RNA: an analysis of 40 intertypic cross-over sequences. Nucleic Acids Res. 16, 11705–11723.

Lentz, T. L. (1990). Review article: The recognition event between virus and host cell receptor, a target for antiviral agents. J. Gen. Virol. 71, 751–766.

Mendelsohn, C., Johnson, B., Lionetti, K. A., Nobis, P., Wimmer, E., Racaniello, V. R. (1986). Transformation of a human poliovirus receptor gene into mouse cells. Proc Natl. Acad. Sci. USA 83, 7845–7849.

Mendelsohn, C., Wimmer, E., Racaniello, V. R. (1989). Cellular receptor for poliovirus: molecular cloning, nucleotide sequence and expression of a new member of the immunoglobulin superfamily. Cell 56, 855–865.

Minor, P. D., Schild, G. C., Ferguson, M., Mackay, A., Magrath, D. I., John, A., Yates, P. J., and Spitz, M. (1982). Genetic and antigenic variation in type 3 polioviruses: Characterization of strains by monoclonal antibodies and Ti oligonucleotide mapping. J. Gen. Vir. 61, 167–176.

Minor, P. D., Schild, G. C., Bootman, J., Evans, D. M. A., Ferguson, M., Reeve, P., Spitz, M., Stanway, F., Cann, A. J., Hauptmann, R., Clarke, L. -D., Mountford, R. C., and Almond, J. W. (1983). Location and primary structure of a major antigenic site for poliovirus neutralization. Nature 301, 674–679.

Minor, P. D., Pipkin, P. A., Hockley, D., Schild, G. C. Almond, J. W. (1984). Monoclonal antibodies which block cellular receptors of poliovirus. Virus Research 1, 203–212.

Minor, P. D., Ferguson, M. and Icenogle, J. P. (1986a). Antigenic and molecular evolution of the vaccine strain of type 3 poliovirus during the period of excretion by a primary vaccinee. J. Gen. Virol. 67, 693–706.

Minor, P. D., Ferguson, M., Evans, D. M. A., Almond, J. W., and Icenogle, J. P. (1986b). Antigenic structure of polioviruses of serotypes 1, 2, and 3. J. Gen. Virol. 67, 1283–1291.

Nobis, P., Zibirre, R., Meyer, G., Kuhne, J., Warnecke, G., Koch, G. (1985). Production of a monoclonal antibody against an epitope on HeLa cells that is the functional poliovirus binding site. J. Gen. Virol. 6, 2563–2569.

Nottay, B. K., Kew, O. M., Hatch, M. H., Heyward, J. T., and Obijeski, J. F., (1981). Molecular variation of type 1 vaccine-related and wild polioviruses during replication in humans. Virology 108, 405–423.

Ohtsuka, E., Matsuki, S., Ikehara, M., Takahasi, Y., and Matsubara, K. (1985). An alternative approach to deoxyoligonucleotides as hybridization probes by insertion of deoxyinosine at ambiguous codon positions. J. Biol. Chem. 260, 2605–2608.

Olive M. D., Al-Mufti, S., Al-Mulla, W., Khan, M. A., Pasca, A., Stanway, G. and AlNakib, W. (1990). Detection and differentiation of picornaviruses in clinical samples following genomic amplification. J. Gen. Virol. 71, 2141–2147.

Page, G. S., Mosser, A. G., Hogle, J. M. Filman, D. J., Rueckert, R. R., and Chow, M. (1988). Three-dimensional structure of poliovirus serotype 1 neutralizing determinants. J. Virol. 62, 1781–1794.

Palmenberg, A. C. (1989). Sequences of picornavirus capsid proteins. In: Molecular Aspects of Picornavirus Infection and Detection. Semler, B. and Ehrenfeld, E. (Eds.), ASM publications, pp. 215–230.

Pan American Health Organization, Washington (1990). Surveillance of wild poliovirus in the Americas. EPI News. 12, 1–3.

Pan American Health Organization, Washington (1991 and 1992). Expanded program on immunization in the Americas. Vol XIV, #5 & #6.

Parvin, J. D., Moscona, A., Pan, W. T., Leider, J. M. and Palese, P. (1986). Measurement of the mutation rates of animal viruses: Influenza A virus and poliovirus type 1. J. Virol. 59, 377–383.

Patriarca, P., Laender, F., Palmeira, G., Couto Oliveira, M. J., Lima Filho, I., de Souza Dantes, M. C., Tenorio Cordeiro, M., Risi, J. B., and Orenstein, W. A. (1988). Randomized trial of alternative formulations of oral poliovaccine in Brazil. Lancet 1, 429–432.

Rico-Hesse, R., Pallansch, M. A., Nottay, B. K., and Kew, O. M. (1987). Geographic distribution of wild poliovirus type 1 genotypes. Virology 160, 311–322.

Rossman, M. G., Arnold, E., Erickson, J. W., Frankenberger, E. A., Griffith, J. P., Hech, H. -J., Johnson, J. E., Kamer, G., Luo, M., Mosser, A. G., Rueckert, R. R., Sherry, B. and Vriend G. (1985). Structure of a human common cold virus and finctional relationship to other picornaviruses. Nature 317, 145–153.

Rossman, M. G. and Palmenberg, A. C. (1989). Conservation of the putative receptor attachment site in picornaviruses. Virol. 164, 373–382.

Shepley, M. P., Sherry, B., Weiner, H. L. (1988). Monoclonal antibody identification of 100 kDa membrane protein in HeLa cells and human spinal cord involved in poliovirus attachment. Proc. Natl. Acad. Sci. USA 85, 7743–7747.

Toyoda, H., Kohara, M., Katoaka, Y., Suganuma, T., Omata, T., Imura, N., and Nomoto, A. (1984). Complete nucleotide sequences of all three poliovirus serotype genomes: Implication for genetic relationship, gene function and antigenic determinants. J. Mol. Biol. 174, 561–585.

Weigers, K., Uhlig, H., and Dernick, R. (1988). Evidence of a complex structure of neutralization antigenic site 1 of poliovirus type 1 Mahoney. J. Virol. 62, 1845–1848.

Weigers, K., Uhlig, H., and Dernick, R. (1989). N-Ag IB of poliovirus type 1: A discontinuous epitope formed by two loops of VP1 comprising residues 96–104 and 141–152. Virology 70, 583–586.

Wiegers, K. J., and Dernick, R. (1992). Molecular basis of antigenic structures of poliovirus: Implications for their evolution during morphogenesis. J. Virol. 66, 4597–4600.

Yang, C. -F., De, L., Holloway, B. P., Pallansch, M. A., and Kew, O. M. (1991). Detection and identification of vaccine-related polioviruses by the polymerase chain reaction. Virus Res. 20, 159–179.

Yang, C. -F., De, L., Yang, Su-Ju, Gomez, J. R., Cruz, J. R., Holloway, B. P., Pallansch, M. A. and Kew, O. M. (1992). Genotype-specific in vitro amplification of sequences of the wild type 3 polioviruses from Mexico and Guatemala. Virus Research 24, 277–296.

What is claimed is:

1. An isolated nucleic acid of from 10–100 nucleotides that selectively hybridizes with and has at least 80% complementarity with a nucleic acid that is fully complementary to a nucleic acid having the nucleotide sequence set forth in the Sequence Listing as SEQ ID NO:23 and which primes poliovirus specific amplification or is a poliovirus specific probe.

2. An isolated nucleic acid of from 10–100 nucleotides that selectively hybridizes with and has at least 80% complementarity with a nucleic acid having the nucleotide sequence set forth in the Sequence Listing as SEQ ID NO:22 and which is a poliovirus specific probe.

3. An isolated nucleic acid of from 10–100 nucleotides that selectively hybridizes with and has at least 80% complementarity with a nucleic acid that is fully complementary to a nucleic acid having the nucleotide sequence set forth in the Sequence Listing as SEQ ID NO:25 and which primes poliovirus specific amplification or is a poliovirus specific probe.

4. An isolated nucleic acid of from 10–100 nucleotides that selectively hybridizes with and has at least 80% complementarity with a nucleic acid having the nucleotide sequence set forth in the Sequence Listing as SEQ ID NO:24 and which is a poliovirus specific probe.

5. An isolated nucleic acid of from 10–100 nucleotides that selectively hybridizes with and has at least 80% complementarity with a nucleic acid that is fully complementary to a nucleic acid having the nucleotide sequence set forth in the Sequence Listing as SEQ ID NO:27 and which primes poliovirus specific amplification or is a poliovirus specific probe.

6. An isolated nucleic acid of from 10–100 nucleotides that selectively hybridizes with and has at least 80% complementarity with a nucleic acid having the nucleotide sequence set forth in the Sequence Listing as SEQ ID NO:26 and which is a poliovirus specific probe.

7. An isolated nucleic acid of from 10–100 nucleotides that selectively hybridizes with and has at least 80% complementarity with a nucleic acid that is fully complementary to a nucleic acid having the nucleotide sequence set forth in the Sequence Listing as SEQ ID NO:28 and which primes poliovirus specific amplification or is a poliovirus specific probe.

8. An isolated nucleic acid of from 10–100 nucleotides that selectively hybridizes with and has at least 80% complementarity with a nucleic acid that is fully complementary to a nucleic acid having the nucleotide sequence set forth in the Sequence Listing as SEQ ID NO:23 and which is a poliovirus specific probe.

9. An isolated nucleic acid of from 10–100 nucleotides that selectively hybridizes with and has at least 80% complementarity with a nucleic acid that is fully complementary to a nucleic acid having the nucleotide sequence set forth in the Sequence Listing as SEQ ID NO:22 and which primes poliovirus specific amplification or is a poliovirus specific probe.

10. An isolated nucleic acid of from 10–100 nucleotides that selectively hybridizes with and has at least 80% complementarity with a nucleic acid that is fully complementary to a nucleic acid having the nucleotide sequence set forth in the Sequence Listing as SEQ ID NO:25 and which is a poliovirus specific probe.

11. An isolated nucleic acid of from 10–100 nucleotides that selectively hybridizes with and has at least 80% complementarity with a nucleic acid that is fully complementary to a nucleic acid having the nucleotide sequence set forth in the Sequence Listing as SEQ ID NO:24 and which primes poliovirus specific amplification or is a poliovirus specific probe.

12. An isolated nucleic acid of from 10–100 nucleotides that selectively hybridizes with and has at least 80% complementarity with a nucleic acid that is fully complementary to a nucleic acid having the nucleotide sequence set forth in the Sequence Listing as SEQ ID NO:27 and which is a poliovirus specific probe.

13. An isolated nucleic acid of from 10–100 nucleotides that selectively hybridizes with and has at least 80% complementarity with a nucleic acid that is fully complementary to a nucleic acid having the nucleotide sequence set forth in the Sequence Listing as SEQ ID NO:26 and which primes poliovirus specific amplification or is a poliovirus specific probe.

14. An isolated nucleic acid of from 10–100 nucleotides that selectively hybridizes with and has at least 80% complementarity with a nucleic acid that is fully complementary to a nucleic acid having the nucleotide sequence set forth in the Sequence Listing as SEQ ID NO:28 and which is a poliovirus specific probe.

\* \* \* \* \*